United States Patent [19]

Schneider et al.

[11] Patent Number: 4,774,370

[45] Date of Patent: Sep. 27, 1988

[54] PROCESS FOR PREPARING 2,2-BIS-(3-NITROPHENYL)-HEXAFLUOROPROPANE, AND 2,2-BIS-(4-CARBOXY-3-NITROPHENYL)-HEXAFLUOROPROPANE OCCURRING AS AN INTERMEDIATE

[75] Inventors: Klaus-Albert Schneider, Hattersheim am Main; Günter Siegemund, Hofheim am Taunus, both of Fed. Rep. of Germany

[73] Assignee: Hoechst Aktiengesellschaft, Frankfurt am Main, Fed. Rep. of Germany

[21] Appl. No.: 76,061

[22] Filed: Jul. 21, 1987

[30] Foreign Application Priority Data

Jul. 23, 1986 [DE] Fed. Rep. of Germany ....... 3624913

[51] Int. Cl.$^4$ .................. C07C 17/33; C07C 21/24; C07C 63/331; C07C 51/373
[52] U.S. Cl. .................... 570/141; 562/435; 570/129
[58] Field of Search ................ 570/141, 129; 562/435

[56] References Cited

U.S. PATENT DOCUMENTS

| 3,310,573 | 3/1967 | Coe | 260/346.3 |
| 3,462,482 | 8/1969 | Farah et al. | 570/142 |
| 3,813,446 | 5/1974 | Jacobs | 570/141 |
| 3,992,459 | 11/1976 | Utne et al. | 570/141 |
| 4,400,546 | 8/1983 | Rammelt et al. | 568/386 |
| 4,649,207 | 3/1987 | Lau et al. | 570/129 |

FOREIGN PATENT DOCUMENTS 1176649 10/1984 Canada ........................ 562/435
0054227 9/1983 European Pat. Off. .

OTHER PUBLICATIONS

K. S. Y. Lau et al., *J. Polymer Sci.*, Polymer Chem. Ed., 20, 2381–2393 (1982).
B. L. Livshitz et al., *Zh. vses. khim. Obshchest.*, 11, 469–470 (1966).
L. Fieser et al., *Lehrbuch der organischen Chemie*, 4th German Ed., 1960, p. 649.

*Primary Examiner*—J. E. Evans

[57] ABSTRACT 2,2-Bis-(3-nitrophenyl)-hexafluoropropane is prepared by oxidation of 2,2-bis-(4-methylphenyl)-hexafluoropropane to 2,2-bis-(4-carboxyphenyl)-hexafluoropropane, nitration of this compound to 2,2-bis-(4-carboxy-3-nitrophenyl)-hexafluoropropane and decarboxylation of the last-mentioned compound.

The process lends to 2,2-bis-(3-nitrophenyl)-hexafluoropropane, free of isomers, in an industrially simple manner and with the use of common chemicals. The compound is a valuable intermediate in the polymer field.

The 2,2-bis-(4-carboxy-3-nitrophenyl)-hexafluoropropane occurring as an intermediate in the process is novel.

7 Claims, No Drawings

PROCESS FOR PREPARING 2,2-BIS-(3-NITROPHENYL)-HEXAFLUOROPROPANE, AND 2,2-BIS-(4-CARBOXY-3-NITROPHENYL)-HEXAFLUOROPROPANE OCCURRING AS AN INTERMEDIATE 2,2-Bis-(3-nitrophenyl)-hexafluoropropane is the compound of the formula

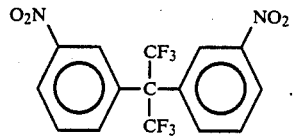

This is mainly an intermediate in the polymer field. Thus, for example, the compound can be reduced to 2,2-bis-(3-aminophenyl)-hexafluoropropane and the bis-amino compound can be condensed with aromatic tetracarboxylic acids or their anhydrides to give valuable polyimides of high chemical and thermal stability. An example of a reaction equation for such a condensation is:

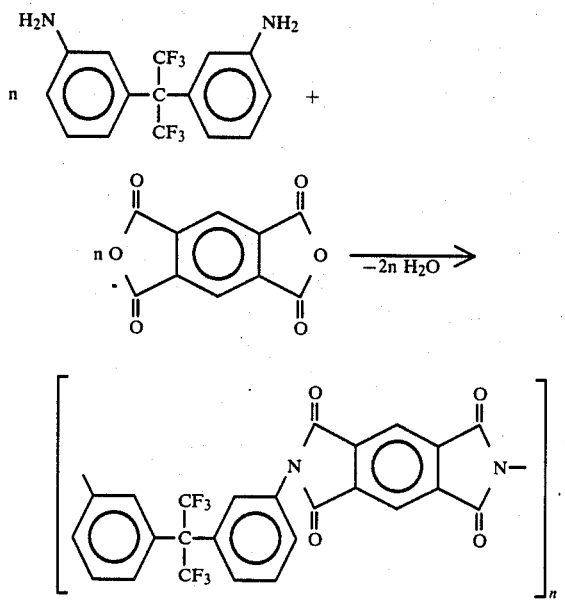

It is known that 2,2-bis-(3-nitrophenyl)-hexafluoropropane can be prepared in a 3-stage process, starting from 2,2-bis-(4-hydroxyphenyl)-hexafluoropropane (K. S. Y. Lau et al., Journal of Polymer Science, Polymer Chemistry Edition, Volume 20, pages 2381–2393 (1982)). In the 1st stage of this process, the starting compound is reacted with trifluoromethanesulfonic acid anhydride to give 2,2-bis-(triflatophenyl)-hexafluoropropane; in the 2nd stage, the last-mentioned compound is catalytically hydrogenated to 2,2-bis-phenylhexafluoropropane and, in the 3rd stage, the 2,2-bisphenylhexafluoropropane is nitrated with $HNO_3/H_2SO_4$ to give the end compound 2,2-bis-(3-nitrophenyl)-hexafluoropropane.

In terms of formulae, the process can be represented as follows:

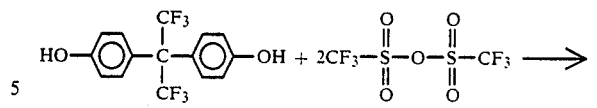

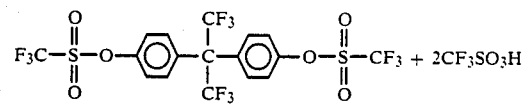

2nd Stage:

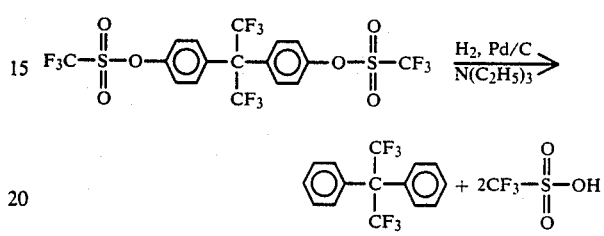

3rd Stage:

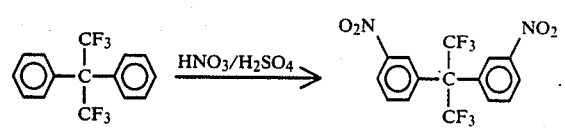

The starting compound of the process—2,2-bis-(4-hydroxyphenyl)-hexafluoropropane—can be obtained, for example, by reacting hexafluoroacetone with phenol in liquid hydrogen fluoride (EP-B-0,054,227).

According to illustrative examples in the abovementioned literature reference, the yields are 96.5% in the 1st stage, 87.6% in the 2nd stage and 90% of theory in the 3rd stage.

In spite of the high yields, the disadvantages of the process are that trifluoromethanesulfonic acid anhydride, which is very expensive and can be handled only with considerable safety precautions, must be used in the 1st stage and that the formation of small proportions of the (undesired) 4-nitro isomers in the 3rd stage can be avoided or reduced only by special measures. The process is therefore not really suitable, especially for industrial implementation.

In an endeavor to provide, for the preparation of 2,2-bis-(3-nitrophenyl)-hexafluoropropane, an improved process, which above all can also be easily carried out industrially, it has now been found that this object can be achieved by starting from 2,2-bis-(4-methylphenyl)-hexafluoropropane, oxidizing this starting compound to 2,2-bis-(4-carboxyphenyl)-hexafluoropropane, nitrating the last-mentioned compound to 2,2-bis-(4-carboxy-3-nitrophenyl)-hexafluoropropane and then finally decarboxylating this nitro compound.

The invention therefore relates to a process for preparing 2,2-bis-(3-nitrophenyl)-hexafluoropropane, which comprises (a) oxidizing 2,2-bis-(4-methylphenyl)-hexafluoropropane to 2,2-bis-(4-carboxyphenyl)-hexafluoropropane, (b) then nitrating the 2,2-bis-(4-carboxyphenyl)-hexafluoropropane to 2,2-bis-(4-carboxy-3-nitrophenyl)-hexafluoropropane and finally (c) decarboxylating the 2,2-bis-(4-carboxy-3-nitrophenyl)-hexafluoropropane.

In terms of formulae, the process can be represented as follows:

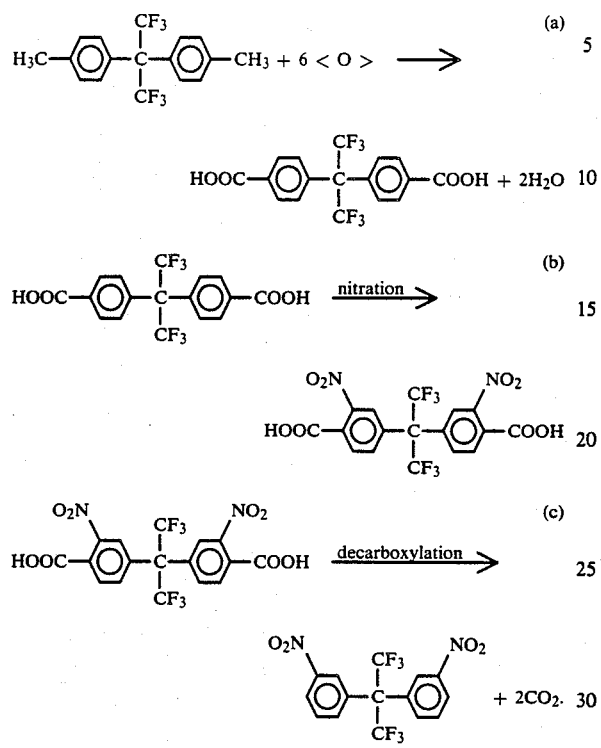

The yields in the individual process stages—and hence also those of the overall process—are of the same order of magnitude as the yields of the individual stages—and of the overall process—according to the literature reference by K. S. Y. Lau et al. (loc. cit.). However, the process according to the invention does not require the use of the expensive and hazardous trifluoromethylsulfonic acid anhydride; rather, the process can be carried out with chemicals all of which are common and can also be readily controlled industrially. Moreover, in this case there is no risk of the formation of undesired 4-nitro isomers, because the 4-position of the phenyl nuclei is occupied by the COOH group during the nitration (in stage b). The end products of the process are therefore absolutely free of isomers.

Although the process stages (a), (b) and (c), taken individually, are known or analogous to known processes, their combination is novel and was not suggested in any way. Based on the state of the art according to K. S. Y. Lau et al. (loc. cit.) which is in fact fairly recent, originating in 1982, it had to be assumed that 2,2-bis-(3-nitrophenyl)-hexafluoropropane could be prepared only in a fairly involved manner with the use of expensive and hazardous chemicals and via rather complicated intermediates (2,2-bis-(4-triflatophenyl)-hexafluoropropane), but not in such a simple and industrially advantageous manner as by the process according to the invention.

The starting compound of the process according to the invention—2,2-bis-(4-methylphenyl)-hexafluoropropane—is obtainable by known methods, for example by reacting hexafluoroacetone with toluene in liquid hydrogen fluoride (B. L. Livsic et al., Z. vses. chim. Obsc. 11 (1966) No. 4, pages 469–470).

The oxidation of the starting compound 2,2-bis-(4-methylphenyl)-hexafluoropropane according to process stage a) is a known reaction. According to B. L. Livsic et al. (loc. cit.), this oxidation is carried out with 20% nitric acid and gives the corresponding dicarboxylic acid—2,2-bis-(4-carboxyphenyl)-hexafluoropropane—in a yield of 82%.

According to U.S. Pat. No. 3,310,573, this oxidation is carried out with $CrO_3$.

Other methods known from the preparation of aromatic carboxylic acids by oxidation of methylbenzenes are also feasible in the present case. However, the method of oxidation with chromium trioxide, as described in U.S. Pat. No. 3,310,573, is here preferred.

The nitration according to process stage (b) is preferably carried out with nitrating acid (=concentrated $HNO_3$/concentrated $H_2SO_4$) in a manner otherwise known for such nitrations.

The preferred temperature range for the nitration is about 40° to 100° C., in particular about 70° to 90° C.

The decarboxylation according to process stage (c) also takes place in principle in a known manner, i.e. in the way known from the decarboxylation of other aromatic carboxylic acids. Preferably, the decarboxylation is carried out in the present case by the method described in Fieser & Fieser, Lehrbuch der organischen Chemie [Textbook of Organic Chemistry], 4th edition, (1960), page 649, paragraph 2.

The method comprises heating the aromatic carboxylic acid dissolved together with a copper catalyst in quinoline. In the present case, however, it is even more advantageous to use pyridine in place of quinoline.

The pyridine can, if desired, also be used as a mixture with other organic nitrogen bases of low volatility. The use of only the other organic nitrogen bases of low volatility—alone or as a mixture with one another—is also possible.

Apart from the quinoline already mentioned, these other organic nitrogen bases of low volatility can, for example, be:

the Cl and methyl derivatives of pyridine and quinoline; isoquinoline, quinoxaline, their Cl and methyl derivatives, etc. Except when used as a solvent, the nitrogen bases can also be used in a quantity which is not sufficient for dissolving the starting compound.

In addition, the presence of catalytically active substances is advantageous in the decarboxylation. The presence of a copper catalyst, in particular of finely disperse copper powder, if appropriate in the presence of copper/chromium oxide $CuCr_2O_4$ also with a small manganese content (in particular about 2% Mn), is preferred.

The quantity of the copper catalyst is not critical in principle; advantageous quantities are about 0.5 to 5% by weight, relative to the 2,2-bis-(4-carboxy-3-nitrophenyl)-hexafluoropropane.

The decarboxylation starts at temperatures at and above 100° C.; higher temperatures of, for example, up to about 250° C. are possible. In general, the process is carried out in the vicinity of the boiling point of the nitrogen base used, in particular at the boiling point of pyridine (115° C.) since pyridine is the preferred nitrogen base.

Working up is carried out in a manner known per se.

The compound 2,2-bis-(4-carboxy-3-nitrophenyl)-hexafluoropropane which occurs as an intermediate in the process according to the invention is novel. By means of the process according to the invention, it provides an overall progressive and advantageous route for the preparation of the known compound 2,2-bis-(3-nitrophenyl)-hexafluoropropane and of the known polymers prepared from the latter.

The invention will now be explained in more detail by the example which follows.

EXAMPLE

(a) Oxidation of 2,2-bis-(4-methylphenyl)-hexafluoropropane 1,500 g (15 mol) of chromium trioxide were added in portions at 80° C. to 664 g (2 mol) of 2,2-bis-(4-methylphenyl)-hexafluoropropane in 6,000 ml of glacial acetic acid. The mixture was stirred overnight at 80°-90° C. and then heated for 2 hours under reflux. The glacial acetic acid was then largely stripped off in vacuo. About 3 liters of water were then added, and the solution was subjected to a steam distillation in order to remove all the acetic acid in this way. After cooling, the reaction mixture was filtered and the filter cake was washed with a little water.

The filter cake was then dissolved in hot soda solution and freed from insoluble residues by filtration. The dicarboxylic acid was liberated by acidifying the filtrate with sulfuric acid. After washing with a little water, 621 g of 2,2-bis-(4-carboxyphenyl)-hexafluoropropane (79% yield) were obtained in this way.

(b) Nitration of 2,2-bis-(4-carboxyphenyl)-hexafluoropropane 392 g (1 mol) of 2,2-bis-(4-carboxylphenyl)-hexafluoropropane were added in portions at a reaction temperature of 70°-80° C. to a nitrating acid composed of 720 ml of 98% nitric acid and 1,008 ml of concentrated sulfuric acid. To complete the reaction, the mixture was stirred at this temperature for a further 3 hours. The reaction mixture was then poured on ice, and the precipitate was filtered off with suction and washed with ice-cold water. After drying of the product thus obtained at 75° C./100 mm Hg in a drying cabinet, 424 g (88% yield) of analytically pure 2,2-bis-(4-carboxy-3-nitrophenyl)-hexafluoropropane were obtained.

Melting point 235°-238° C.

IR (KBr): $\nu=3,350-2,400$ cm$^{-1}$ (COOH), 1,720 cm$^{-1}$ (C=O), 1,540, 1,360 cm$^{-1}$ (NO$_2$), 1,305-1,180 cm$^{-1}$ (CF$_3$).

$^1$H (DMSO): $\delta=7.9$ (mc, 6H, aromatic).

$^{13}$C (DMSO): $\delta=165.1$ (C=O; not uncoupled: dd, $^2J_{C,H}=4$ Hz, $^3J_{C,H}=1$ Hz), 148.4 (aromatic; not uncoupled: mc), 134.7 (aromatic; not uncoupled: d, $^2J_{C,H}=9$ Hz), 134.5 (aromatic; not uncoupled: dd, $^1J_{C,H}=168$ Hz, $^2J_{C,H}=7$ Hz), 130.9 (aromatic; not uncoupled: d, $^1J_{C,H}=171$ Hz), 129.2 (aromatic; not uncoupled: dd, $^2J_{C,H}=5$ Hz, $^2J_{C,H}=8$ Hz), 125.0 (aromatic; dd, $^1J_{C,H}=169$ Hz, $^2J_{C,H}=6$ Hz), 123.2 (q, $^1J_{C,F}=279$ Hz, CF$_3$).

$^{19}$F (DMSO) $\delta=-62.8$ (CF$_3$).

C$_{17}$H$_8$F$_6$N$_2$O$_8$: Calculated: C 42.3 F 1.7 F 23.6 N 5.8. (482.2) Found: C 42.5 H 1.6 F 23.3 N 5.9.

(c) Decarboxylation of 2,2-bis-(4-carboxy-3-nitrophenyl)-hexafluoropropane

A reaction mixture composed of 724 g (1.5 mol) of 2,2-bis-(4-carboxy-3-nitrophenyl)-hexafluoropropane, 2,100 ml of pyridine, 20 g of Cu powder and 10 g of CuCr$_2$O$_4$+2% Mn was heated under reflux until CO$_2$ from the reaction was no longer detectable by IR spectroscopy in the exit air.

The reaction mixture was then separated from the solid constituents by filtration, and the major part of the pyridine was removed from the filtrate by means of a vacuum distillation. The remaining residue was dissolved in CH$_2$Cl$_2$, and half-concentrated hydrochloric acid was added in order to remove the residual pyridine. After the aqueous phase had been separated off and the organic phase had been washed until neutral, the organic phase was dried over MgSO$_4$. After stripping off the solvent and recrystallizing the resulting crude product from ethanol, 463 g (78% yield) of the dinitro compound were obtained.

Melting point 116°-119° C. p IR (KBr) $\nu=1,550$, 1,360 cm$^{-1}$ (NO$_2$), 1,310-1,160 cm$^{-1}$ (CF$_3$).

$^1$H (CDCl$_3$): $\delta=8.3$ (mc, 4H, aromatic), 7.7 (mc, 4H, aromatic).

$^{13}$C (CDCl$_3$): $\delta=148.5$, 135.6, 134.3, 129.9, 125.1, 124.8 (aromatic), 122.6 (q, $^1J_{C,F}=298$ Hz, 2CF$_3$), 64.6 (mc, C(CF$_3$)$_2$).

$^{19}$F (DMSO): $\delta=-64.2$ (CF$_3$).

C$_{15}$H$_8$F$_6$N$_2$O$_4$: Calculated: C 45.7 H 2.0 F 28.9 N 7.1 O 16.2 (394.2) Found: C 45.8 H 2.2 F 28.6 N 7.1 O 16.0.

What is claimed is:

1. A process for preparing 2,2-bis-(3-nitrophenyl)-hexafluoropropane, which comprises
   (a) oxidizing 2,2-bis-(4-methylphenyl)-hexafluoropropane to 2,2-bis-(4-carboxyphenyl)-hexafluoropropane,
   (b) then nitrating the 2,2-bis-(4-carboxyphenyl)-hexafluoropropane to 2,2-bis-(4-carboxy-3-nitrophenyl)-hexafluoropropane and finally
   (c) decarboxylating the 2,2-bis-(4-carboxy-3-nitrophenyl)-hexafluoropropane.

2. The process as claimed in claim 1, wherein the oxidation in stage (a) is carried out with chromium trioxide.

3. The process as claimed in claim 1, wherein the nitration in stage (b) is carried out with nitrating acid at temperatures between about 40° and 100° C.

4. The process as claimed in claim 1, wherein the decarboxylation in stage (c) is carried out in the presence of organic nitrogen bases of low volatility and of a copper catalyst at temperatures of about 100°-250° C.

5. 2,2-Bis-(4-carboxy-3-nitrophenyl)-hexafluoropropane of the formula

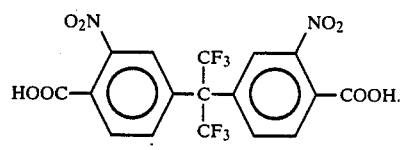

6. The process as claimed in claim 3, wherein said temperatures are between about 70° and 90° C.

7. The process as claimed in claim 4, wherein said temperatures are at the boiling point of the nitrogen bases used.

* * * * *